United States Patent
Mukundan et al.

(10) Patent No.: US 6,656,336 B2
(45) Date of Patent: Dec. 2, 2003

(54) METHOD FOR FORMING A POTENTIAL HYDROCARBON SENSOR WITH LOW SENSITIVITY TO METHANE AND CO

(75) Inventors: Rangachary Mukundan, Santa Fe, NM (US); Eric L. Brosha, Los Alamos, NM (US); Fernando Garzon, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/158,997

(22) Filed: May 30, 2002

(65) Prior Publication Data
US 2002/0185376 A1 Dec. 12, 2002

Related U.S. Application Data

(63) Continuation-in-part of application No. 09/770,928, filed on Jan. 25, 2001, now abandoned.

(51) Int. Cl.[7] .................. G01N 27/407; B29C 43/00; B30B 1/00
(52) U.S. Cl. .................. 204/424; 204/421; 204/426; 100/2; 100/3; 100/35; 264/109; 264/122; 264/618; 264/642
(58) Field of Search .................. 204/421–429; 205/783.5–785; 100/2, 3, 35; 264/109, 122, 618, 642, 643

(56) References Cited

U.S. PATENT DOCUMENTS

| | | | |
|---|---|---|---|
| 3,074,143 A | 1/1963 | Smith | 25/156 |
| 3,723,589 A | 3/1973 | Kennedy | 264/101 |
| 4,220,517 A | 9/1980 | Niwa et al. | 204/195 S |
| 4,277,323 A | 7/1981 | Muller et al. | 204/195 S |
| 4,304,652 A | 12/1981 | Chiba et al. | 204/195 S |
| 4,478,590 A | 10/1984 | Rychlewski | 445/50 |
| 4,502,939 A | 3/1985 | Holfelder et al. | 204/429 |
| 4,614,628 A | 9/1986 | Hsu et al. | 264/61 |
| 4,735,666 A | 4/1988 | Mase et al. | 156/89 |
| 4,786,374 A | 11/1988 | Worrell et al. | 204/1 T |
| 4,820,663 A | 4/1989 | Mehrotra et al. | 501/87 |
| 5,215,643 A | 6/1993 | Kusanagi et al. | 204/412 |
| 5,543,025 A | 8/1996 | Garzon et al. | 204/425 |
| 6,019,881 A | 2/2000 | Kurosawa et al. | 204/424 |
| 6,103,080 A | 8/2000 | Pham et al. | 204/424 |

OTHER PUBLICATIONS

Miura et al., "Mixed Potential Type $NO_x$ Sensor Based on Stabilized Zirconia and Oxide Electrode," J. Electrochem. Soc. vol. 143, No. 2, Feb. 1996.

Hibino et al., "High–Temperature Hydrocarbon Sensors Based on a Stabilized Zirconia Electrolyte and Metal Oxide Electrodes," Electrochemical and Solid State Letters, 2 (12), pp. 651–653, 1999. Month Unavailable.

Mukundan et al., "A Mixed–Potential Sensor Based on a $Ce_{0.8}Gd_{0.2}O_{1.9}$ Electrolyte and Platinum and Gold Electrodes," Journal of The Electrochemical Society, 147 (4), pp. 1583–1588, 2000. Month Unavailable.

(List continued on next page.)

Primary Examiner—T. Tung
(74) Attorney, Agent, or Firm—Ray C. Wilson

(57) ABSTRACT

A hydrocarbon sensor is formed with an electrolyte body having a first electrolyte surface with a reference electrode depending therefrom and a metal oxide electrode body contained within the electrolyte body and having a first electrode surface coplanar with the first electrolyte surface. The sensor was formed by forming a sintered metal-oxide electrode body and placing the metal-oxide electrode body within an electrolyte powder. The electrolyte powder with the metal-oxide electrode body was pressed to form a pressed electrolyte body containing the metal-oxide electrode body. The electrolyte was removed from an electrolyte surface above the metal-oxide electrode body to expose a metal-oxide electrode surface that is coplanar with the electrolyte surface. The electrolyte body and the metal-oxide electrode body were then sintered to form the hydrocarbon sensor.

7 Claims, 5 Drawing Sheets

OTHER PUBLICATIONS

Mukundan et al., "Ceria–Electrolyte–Based Mixed Potential Sensors for the Detection of Hydrocarbons and Carbon Monoxide," Electrochemical and Solid State Letters, 2 (8), pp. 412–414, 1999. Month Unavailable.

Williams et al., "Solid Electrolyte Mixed Potential Phenomena," Studies in Inorganic Chemistry, vol. 3, pp 275–278, 1982. Month Unavailable.

Miura et al., "Highly Selective CO Sensor Using Stabilized Zirconia and a Couple of Oxide Electrodes," Sensors and Actuators B 47 pp. 84–91, 1998. Month Unavailable.

Li et al., "High–Temperature Carbon Monoxide Potentiometric Sensor," J. Electrochem. Soc. vol. 140, No. 4, pp. 1068–1073, Apr. 1993.

METHOD FOR FORMING A POTENTIAL HYDROCARBON SENSOR WITH LOW SENSITIVITY TO METHANE AND CO

RELATED CASES

This application is a continuation-in-part of U.S. patent application Ser. No. 09/770,928, filed Jan. 25, 2001 now abandoned.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to hydrocarbon sensors, and, more particularly, to solid state hydrocarbon sensors having metal and metal oxide electrodes.

BACKGROUND OF THE INVENTION

Mixed-potential sensors based on oxygen-ion conducting electrolytes have been studied since D. E. Willams et. al. demonstrated the working of a "Pt/YSZ/Au" CO-sensor operating at $T \leq 400°$ C. Since that time several metal and metal-oxide electrodes have been used to design various mixed-potential sensors for the detection of CO, $NO_x$, and hydrocarbons. Although all these sensors do give a response in the presence of unsaturated hydrocarbons and/or CO, their lack of stability, reproducibility and selectivity have hindered the commercial development of sensors based on this technology.

The first generation of mixed potential sensors (D. E. Willams et. al.) used Gold (Au) and Pt electrodes on a stabilized zirconia electrolyte. The Au electrode in these devices was painted onto the electrolyte. The morphology of this electrode was not easy to reproduce from sensor to sensor, and also the morphology changes with time as the sensor was being operated at elevated temperatures. In order to solve this problem, two other approaches have been tried. The first involved the use of various alloys of Au and other metals with higher melting point than that of Au. The second involved the use of various oxides mixed in with the Au in order to create a cermet electrode.

In the present invention, the Au electrode is replaced with a conductive oxide electrode. The refractory nature of the oxide electrode ensures its morphological stability and the sensor is capable of withstanding temperatures as high as 850° C. Moreover, the use of a sintered ceramic pellet (instead of a thin film of oxide) provides excellent control of the electrode area and 3-phase region thus improving the sensor-to-sensor reproducibility.

The mixed-potential that is developed at an electrode/electrolyte interface in the presence of a reducing gas such as CO or hydrocarbons is fixed by the rates of reduction and oxidation of the oxygen and the reducing gas respectively:

(Eqn. 1)

(Eqn. 2)

Both these electrochemical reactions occur at the electrode/electrolyte/gas 3-phase interface and the mixed-potential is that potential $V_0$ at which the rates of these two reactions are exactly equal. That is, the current due to the reduction reaction (Equation 1) equals the current due to the oxidation reaction (Equation 2) when the over-potential of these two reactions equals the mixed potential. The speed (response time) of these sensors will be determined by the time it takes for the two reactions to reach steady state.

In the prior art, a dense YSZ electrolyte is used as the substrate and a metal or metal oxide electrode is deposited on top of this electrolyte. The length of the active 3-phase interface is controlled by the morphology of the electrode. A highly porous electrode results in better gas access and more 3-phase interface, whereas a denser electrode leads to poorer gas access and lesser 3-phase interface. One drawback of this type of arrangement is that the gas has to meander through the pores of a catalytically active material (the electrode) before reaching the 3-phase interface where the reduction and oxidation reactions occur. Hence, the hydrocarbons (or other reducing gases) are heterogeneously oxidized at the metal (or metal oxide) electrode before they reach the 3-phase interface with the electrolyte, with a concomitant loss in sensor sensitivity and response time.

These attributes of the prior art are addressed by the present invention, and various advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention includes a hydrocarbon sensor with an electrolyte body having a first electrolyte surface with a reference electrode depending therefrom and a metal oxide electrode body contained within the electrolyte body and having a first electrode surface coplanar with the first electrolyte surface. The sensor is formed by forming a sintered metal-oxide electrode body and placing the metal-oxide electrode body within an electrolyte powder. The electrolyte powder with the metal-oxide electrode body is pressed to form a pressed electrolyte body containing the metal-oxide electrode body. The electrolyte is removed from an electrolyte surface above the metal-oxide electrode body to expose a metal-oxide electrode surface that is coplanar with the electrolyte surface. The electrolyte body and the metal-oxide electrode body are then sintered to form the hydrocarbon sensor. In a particular aspect of the present invention, the response time of the sensor is improved by sintering at a temperature effective to produce a density less than about 81% of theoretical maximum density.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

This invention is a mixed-potential sensor for the detection of non-methane hydrocarbons (NMHCs). The sensor utilizes a stabilized-zirconia electrolyte, and platinum (Pt) and perovskite-type oxide electrodes. The Pt electrode acts as a pseudo-reference electrode while the oxide electrode gives the mixed potential in the presence of reducing-gases. The selectivity of the device is achieved by the proper selection of the oxide electrode, while the stability of the device is achieved by the precise control of the surface area (SA) of the electrode and the 3-phase interface region (3PA) (gas-electrolyte-electrode) of the sensor. In accordance with one aspect of the present invention, the oxide electrode is $La_{1-x}A_xCrO_3$, where A is Sr, Ca, or Mg, $0 \leq x \leq 0.5$.

By controlling the ratio of the SA to the 3PA, the rates of the heterogeneous catalysis and electrochemical catalysis are controlled for any particular electrode used. Thus, by proper selection of the electrode material and electrode dimensions, the magnitude of sensor response to any particular gas species can be amplified (selectivity). Moreover the design of the sensor assures that the SA and 3PA are stable over time and can be easily reproduced from sensor to sensor which ensures the stable and-reproducible nature of the sensor response.

The specific approach involves the following steps:
1) Sintering the metal-oxide electrode to form a dense ceramic.
2) Cutting the ceramic to size (area of one of the sides=SA).
3) Co-pressing the ceramic pellet along with the electrolyte powder.
4) Polishing off the excess electrolyte powder in order to expose the oxide electrode.
5) Sintering or partial-sintering of the resultant electrode/electrolyte structure in order to give mechanical strength and sufficient ionic-conductivity to the electrolyte.
6) Applying a current collector electrode on the ceramic electrode surface.

The stated approach produces one of the electrodes. The other electrode can either be made in a similar manner with another oxide of different composition or with a metal wire.

Figure 1A:
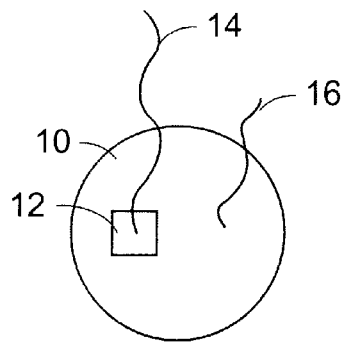
FIGS. 1A and 1B are top and cross-section views, respectively of a sensor according to one embodiment of the present invention.
Figure 1B:
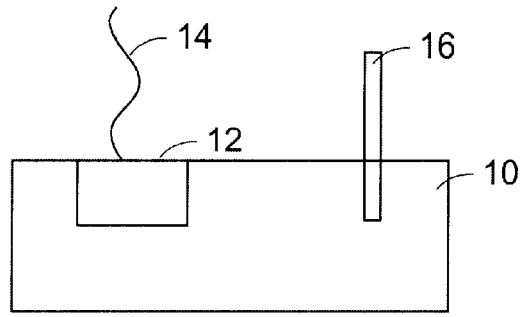

As shown in FIGS. 1A and 1B, specific test cells were fabricated in accordance with the above procedure using $La_{0.8}Sr_{0.2}CrO_3$ as the oxide electrode 12, yttria-stabilized zirconia (YSZ) as the electrolyte 10, and Pt as the reference electrode 16. A lead wire 14 was attached to oxide electrode 12. A $La_{0.8}Sr_{0.2}CrO_3$ powder was obtained from Praxair® and was pressed into a pellet and sintered at 1550–1650° C. for 10 hours in order to form a dense (>60% of theoretical density) ceramic. The ceramic pellet was cut into smaller pellets with dimensions 0.2 cm×0.3 cm×0.2 cm. The pellet was buried in YSZ powder (having a surface area of 33.2 $m^2/gm$) and pressed uniaxially at 1500 lbs in a ½"-¾" diameter die for 5 minutes. The excess YSZ was removed from the surface of the oxide electrode pellet using a razor blade. Once a clear electrode/electrolyte interface was exposed, the pellet was sintered at 1000–1100° C. for 10–24 hours. The resulting pellet was about 60% of theoretical density. A 0.004" diameter Pt wire was fixed onto the surface of the oxide electrode using a small drop of Pt paint. The other electrode was a Pt (0.01" diameter) wire buried into the YSZ-electrolyte. The sensor was fixed to Pt (0.01" diameter) leads and was heated to 400–600° C. in various gas atmospheres in order to test the sensor response.

Figure 2:
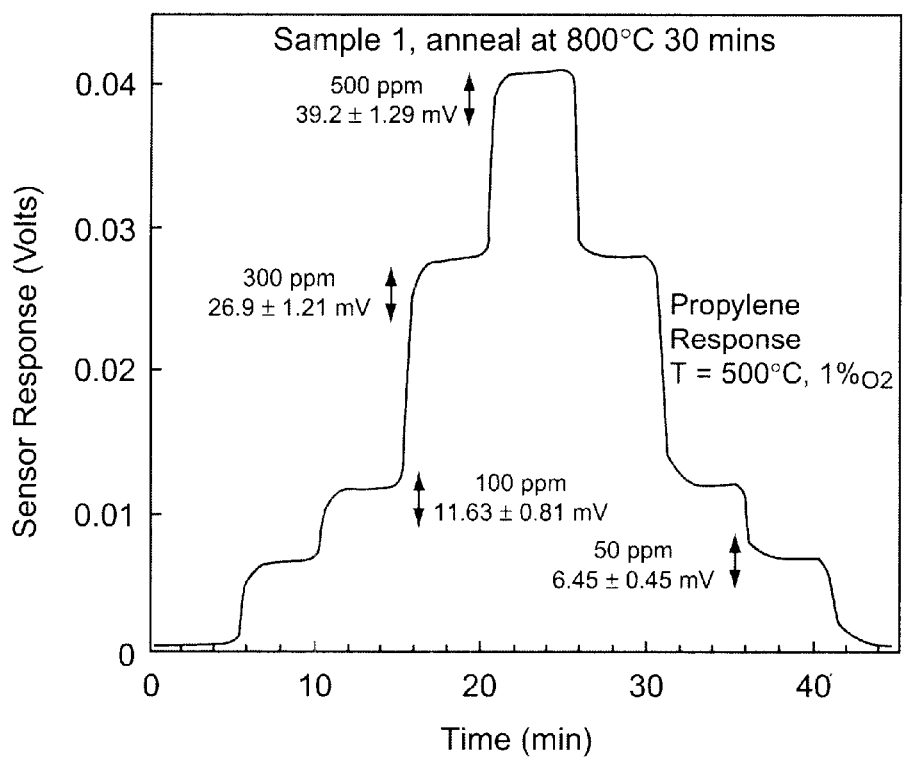
FIG. 2 graphically depicts sensor response to propylene concentration in 1% $O_2$ at T=500° C.
Figure 3:
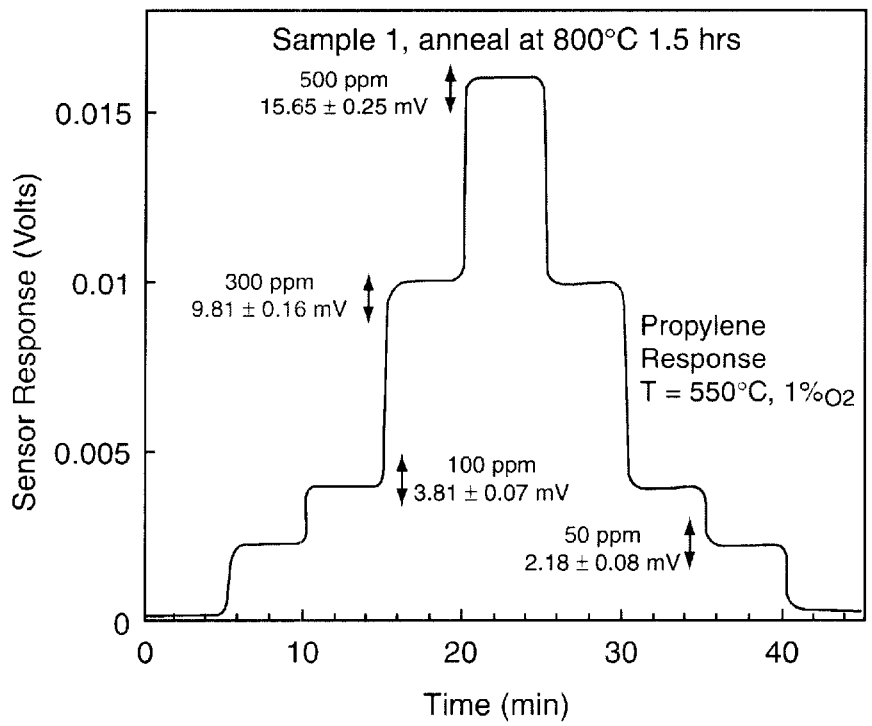
FIG. 3 graphically depicts sensor response to propylene concentration in 1% $O_2$ at T=550° C. over several days.

The first sensor was annealed at 800° C. for 30 minutes in order to stabilize the Pt electrodes and was then cooled to 500° C., where the sensor was tested. The sensor response to propylene concentration in a 1% $O_2$ test gas (as used herein, all % numbers are volume %) at T=500° C. is shown in FIG. 2. The sensor response was very reproducible and was stable with time for at least 10 days (maximum deviation was <10%). The sensor response to 500 ppm propylene was about 40 mV at T=500° C. and had a response time of about 50 sec. In order to improve the response time, the operating temperature of the sensor was raised to 550° C. The sensor response to propylene concentration in a 1% 02 test gas at T=550° C. is shown in FIG. 3. The response to 500 ppm propylene was about 15 mV with a response time of about 25 sec. The sensor response at T=550° C. was also found to be stable for a period of at least 3 days. The sensor response time could be further improved by using a testing system with a lower volume (t<10 sec) and/or higher space velocities of the test gas.

Figure 4:
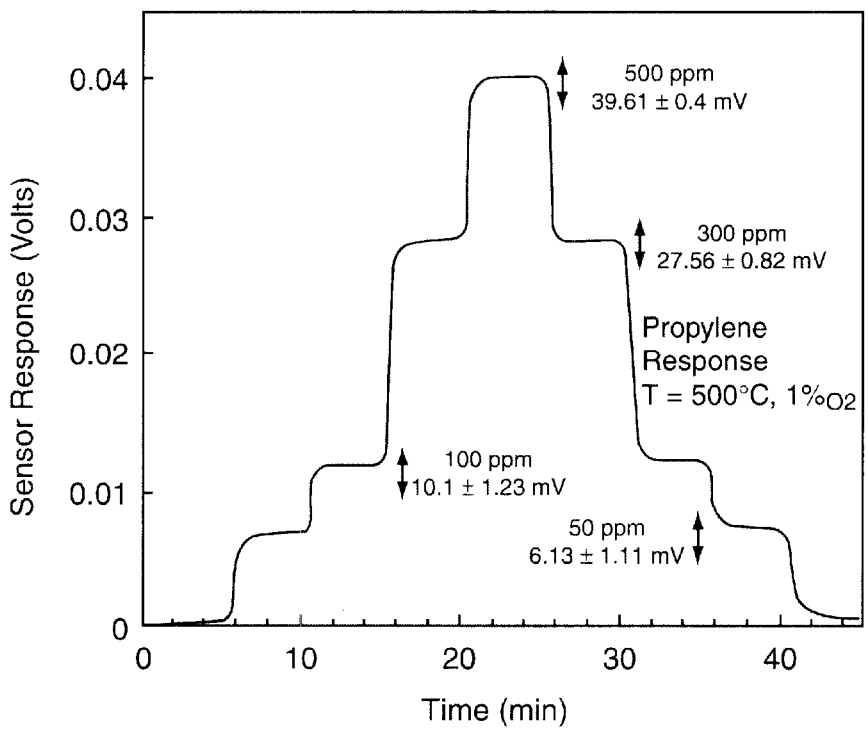
FIG. 4 graphically depicts the response of two different sensors to propylene concentration in 1% $O_2$.

In order to test the sensor—sensor reproducibility, another identical sensor was made and tested at 500° C. The sensor response of this sensor (sample 2) was in good agreement with that of the first sensor (sample 1) as shown in FIG. 4. For example, the variation in response between the 2 sensors for 500 ppm propylene was about 1%.

Figure 5:
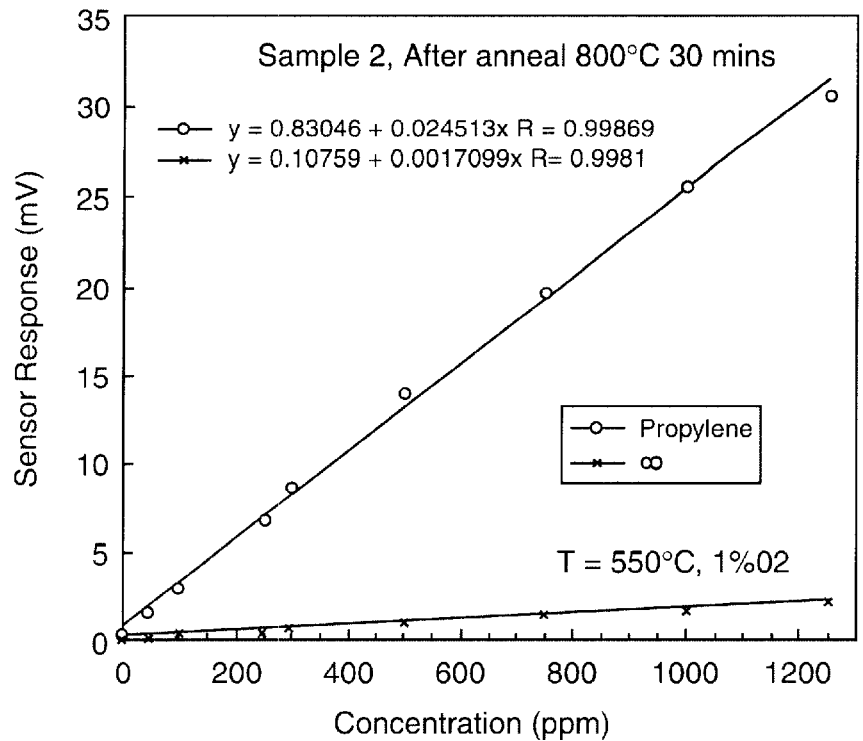
FIG. 5 graphically depicts the sensor response to propylene and to CO in 1% $O_2$ at T=550° C.
Figure 6:
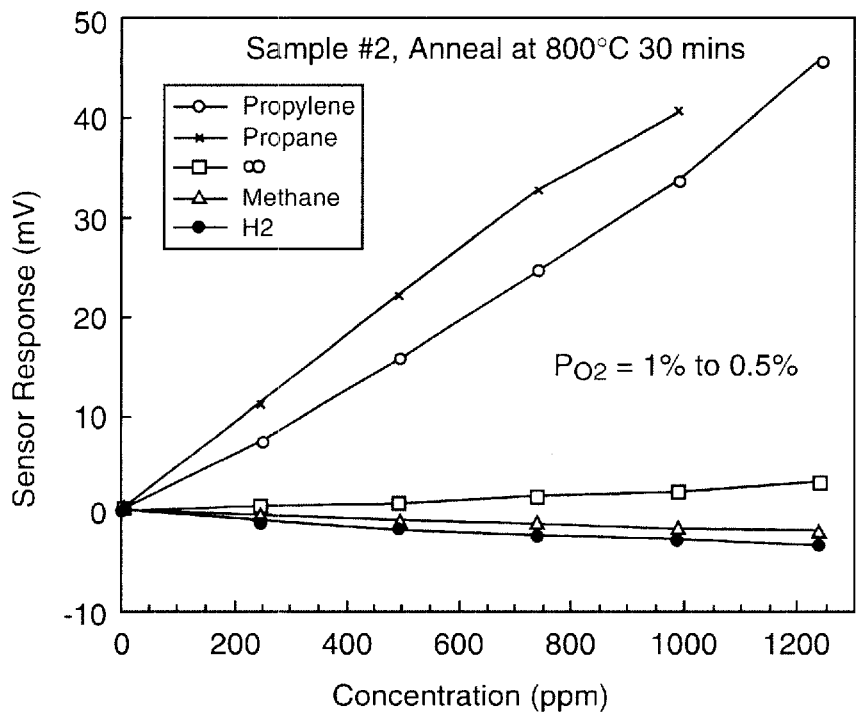
FIG. 6 graphically depicts the sensor response to various gases in 1% $O_2$ at T=550° C.

In order to test for interference from other gases, the sensor was exposed to varying concentration of CO (primary interference gas) in a 1% $O_2$ background. The response to propylene and CO in 1% $O_2$ at T=550° C. is compared in FIG. 5. This sensor not only shows a linear response to varying concentration of the analyzed gas but also has very good selectivity to propylene relative to CO (14 times more sensitive to propylene). The sensor response to other gases commonly present in the exhaust (propane, $H_2$, and methane) was also tested. However the oxygen concentration was not kept constant during these tests and was allowed to vary from 1% $O_2$ (for 0 ppm of test gas) to 0.5% $O_2$ (for 1250 ppm of test gas). The results (FIG. 6) indicate that the sensor responds primarily to NMHCs (propylene and propane) and shows little interference from other gases.

Another design was also tested in order to improve the current collection from the chromate electrode. A Pt wire (0.01" diameter) was buried in the chromate powder before it was pressed into a pellet and was sintered along with the pellet in order to make a Pt wire current collector that was both stable and robust. This sensor had a very similar response to those described above indicating that the various methods of current collection could be employed and that the sensor response is primarily controlled by the perovskite-type oxide. Moreover this sensor also had a response time (to 90% of level) of ≈10 sec.

There are two significant improvements of the present sensor over existing technology: the sensor response is stable over time and is reproducible from sensor to sensor; and the sensor response is highly selective to non-methane hydrocarbons.

The mixed-potential sensor can be used to sense the amount of NMHC emitted by any combustion, and, more particularly, in the tailpipe emissions of an automobile. This would help the auto-manufacturers test the efficiency of the catalytic converter. The current technology utilizes a two oxygen sensor approach where one oxygen sensor is placed in the exhaust upstream of the catalytic converter and the other downstream. The difference in the signal between the two sensors when the engine is cycled through stoichiometry is a measure of the oxygen capacity in the catalytic converter. The above method to determine the health of the converter is indirect (does not measure the actual conversion efficiency) and moreover will work only when the engine is cycled through stoichiometry.

The sensor according to the present invention can provide a direct measure of the catalyst efficiency because the sensor can be placed downstream of the converter and the sensor provides a measure of the actual amount of NMHC coming out of the tailpipe. Moreover the sensor works in high oxygen concentrations ($\approx 1\%$) which makes it ideal for operation in the exhaust of a lean-burn engine.

As described above, one aspect of the present invention is a solid electrode embedded in a porous YSZ electrolyte. In another aspect of this invention, the 3-phase interface is increased by increasing the porosity of the electrolyte. It is well known that the commonly used electrode materials, e.g., precious metals, perovskite or transition-metal oxides and spinels, have much greater heterogeneous catalysis rates than the YSZ electrolyte. By increasing the porosity of the electrolyte material, the gases meander through the YSZ electrolyte instead of the electrode with a concomitant decrease in the heterogeneous catalysis that occurs before the gases reach the 3-phase interface. Hence, the response time of the sensors is improved by increasing the 3-phase interface without losing the sensor response due to heterogeneous catalysis on the porous electrode.

The effect of varying porosity of the electrolyte on the sensor response was illustrated by preparing several sensors with differing electrolyte density. This was achieved by sintering the YSZ electrolyte at various temperatures. The starting YSZ powder was obtained from Praxair as agglomerated powder at 10.5 m$^2$/gm surface area. The YSZ electrolyte was sintered at 1050° C., 1100° C. and 1200° C., producing electrolyte materials that were approximately 81%, 86% and 90% of theoretical density, respectively. Two different sensors (given in Table 1) were studied in order to illustrate the effect of porosity (density) on the response time of these sensors.

TABLE 1

| SAMPLE | Electrode (+ve) | Electrode (−ve) | Electrolyte | Sintering Temp.(° C.) | Sintering Time (hrs) |
|---|---|---|---|---|---|
| Sensor A | Pt (d = 0.01") | La$_{0.7}$Sr$_{0.3}$CrO$_3$ | YSZ | 1050 1200 | 10 |
| Sensor B | Pt (d = 0.01") | La$_{0.8}$Sr$_{0.2}$CrO$_3$ | YSZ | 1050 1200 | 10 |

Figure 7:
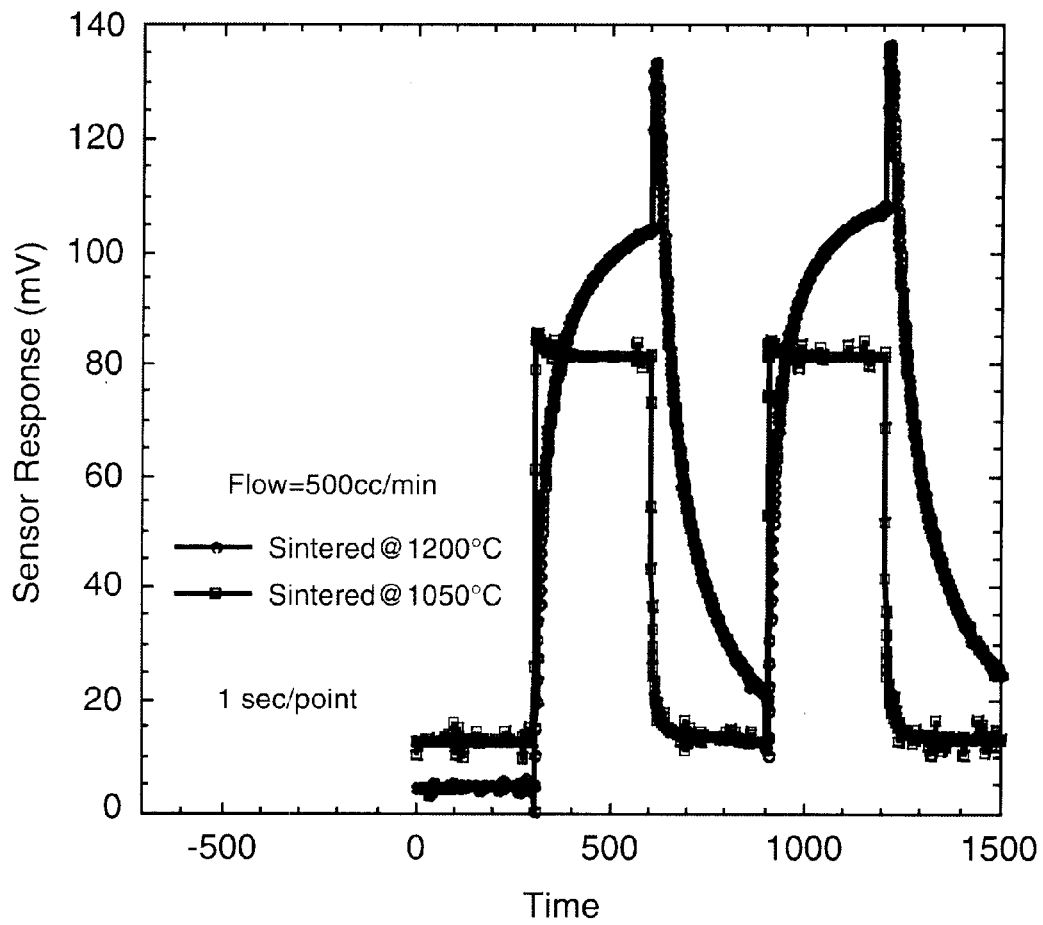
FIG. 7 graphically compares the response characteristics in 1% $O_2$ at 600° C. of a first sensor according to one aspect of the present invention after sintering at 1050° C. and after sintering at 1200° C.

Sensors A and B were initially sintered at 1050° C. for 10 hours and their response to propylene was evaluated under various conditions. Then, these two sensors were sintered again at 1200° C. and their propylene response was reevaluated. FIG. 7 shows the response of sensor A to 500 ppm of propylene at 600° C. in 1% O$_2$. It is seen that the sensor response to 500 ppm of propylene is increased from 80 mV to $\approx$110 mV when the sintering temperature is increased from 1050° C. to 1200° C. However, the response time increases from 3 sec to $\approx$140 sec as the sintering temperature is increased. This shows that the response time can be dramatically improved by sintering the YSZ electrolyte at a lower temperature. The better response time is due to a sensor body with higher porosity.

Figure 8:
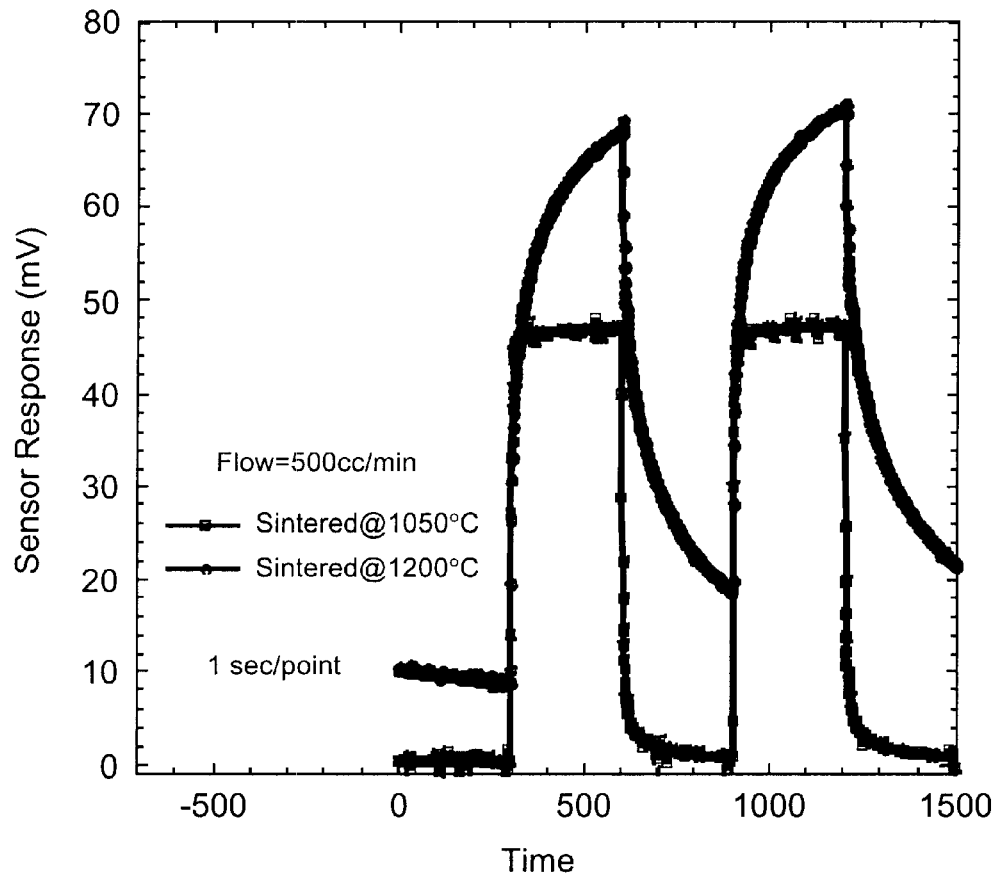
FIG. 8 graphically compares the response characteristics in 1% $O_2$ at 650° C. of a second sensor according to one aspect of the present invention after sintering at 1050° C. and after sintering at 1200° C.

FIG. 8 shows similar response curves obtained for Sensor B, which was operated at a temperature of 650° C. The higher operating temperature compared to that of Sensor A results in a lower sensor response due to greater heterogeneous catalysis at this higher temperature. For example, the sensor response to 500 ppm of propylene is only 45 mV as compared to a response of 80 mV for Sensor A. However, the trends in the response times observed are identical and the response time is increased from 5 sec to $\approx$160 sec as the sintering temperature is increased from 1050° C. to 1200° C.

Accordingly, the sensor response time is decreased by increasing the porosity (or decreasing the density) of the electrolyte. The more porous the electrolyte, the faster is the gas access to the YSZ/electrode interface resulting in faster kinetics of the reduction and oxidation reactions. Moreover, an increase in the operating temperature and the flow rate of the gas also resulted in faster gas access and hence faster sensor response. By optimizing the various parameters, a sensor response of approximately 1 sec was obtained.

It will be appreciated from the above description that the resulting theoretical density and concomitant porosity is a function of the beginning YSZ powder morphology and sintering temperature. That is, the un-agglomerated powders (e.g. a powder having 33.2 m$^2$/gm surface area as the first group of sensors) will maintain a relatively low density (higher porosity) at a given sintering temperature than the spherical agglomerated Praxair powders (having a 10.5 m$^2$/gm surface area as in samples A and B).

To obtain a fast response time, it is desired that the YSZ electrolyte be sintered at a temperature effective to produce a density less than about 81% of theoretical density. The minimum acceptable density is a density that maintains the mechanical integrity of the sintered material. In the first set of sensors, the YSZ electrolyte was sintered at 1000° C.–1100° C. to produce a density of about 60% of theoretical density. Sensors A and B were sintered at 1050° C. to produce a density of 81% theoretical density; at 1100° C. to produce a density of 86% of theoretical density; and at 1200° C. to produce a density of 90% of theoretical density.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for forming a hydrocarbon sensor comprising:

forming a sintered metal-oxide electrode body;

placing the metal-oxide electrode body within an electrolyte powder;

pressing the electrolyte powder with the metal-oxide electrode body to form a pressed electrolyte body containing the metal-oxide electrode body;

removing electrolyte from an electrolyte surface above the metal-oxide electrode body to expose a metal-oxide electrode surface that is coplanar with the electrolyte surface; and sintering the electrolyte body with the metal-oxide electrode body to form the hydrocarbon sensor.

2. The method of claim 1, where the metal oxide electrode body is formed from $La_{1-x}A_xCrO_3$, where A is selected from the group consisting of Sr, Ca, and Mg, and $0 \leq x \leq 0.5$.

3. The method of claim 2, where the A is Sr and x=0.2.

4. The method of claim 1 where the electrolyte is yttria-stabilized zirconia.

5. The method of claim 4, where the metal oxide electrode body is formed from $La_{1-x}A_xCrO_3$, where A is selected from the group consisting of Sr, Ca, and Mg, and $0 \leq x \leq 0.5$.

6. The method of claim 5, where A is Sr and x=0.2.

7. The method of claim 6, wherein the electrolyte body with the metal-oxide electrode body is sintered at a temperature effective to produce a density less than about 81% of theoretical density.

* * * * *